United States Patent [19]

Yamaguchi et al.

[11] Patent Number: 5,243,104
[45] Date of Patent: Sep. 7, 1993

[54] PROCESS FOR PREPARING CHLOROTRIFLUOROETHYLENE

[75] Inventors: Fumihiko Yamaguchi; Tatsuya Otsuka; Koutarou Nakagawa, all of Settsu, Japan

[73] Assignee: Daikin Industries Limited, Osaka, Japan

[21] Appl. No.: 886,928

[22] Filed: May 22, 1992

[30] Foreign Application Priority Data

May 24, 1991 [JP] Japan .................. 3-120131

[51] Int. Cl.$^5$ ............................................. C07C 17/02
[52] U.S. Cl. .................................................. 570/153
[58] Field of Search ............................ 570/175, 153

[56] References Cited

U.S. PATENT DOCUMENTS

| | | | |
|---|---|---|---|
| 2,343,252 | 3/1944 | Benning | 570/175 |
| 2,365,516 | 12/1944 | Benning | 570/175 |
| 2,393,304 | 1/1946 | Benning | 570/175 |

Primary Examiner—Alan Siegel
Attorney, Agent, or Firm—Birch, Stewart, Kolasch & Birch

[57] ABSTRACT

Chlorotrifluoroethylene is prepared in high yield by reacting tetrafluoroethylene with hydrogen chloride in the presence of a metallic catalyst without using 1,1,2-trichlorotrifluoroethylene, which destroys the ozone layer.

22 Claims, No Drawings

PROCESS FOR PREPARING CHLOROTRIFLUOROETHYLENE

BACKGROUND OF THE INVENTION

1. Field of the Invention

The present invention relates to a process for preparing chlorotrifluoroethylene (hereinafter referred to as "CTFE") which is one of the commercially important monomers.

2. Description of Related Art

Hitherto, various methods for preparing CTFE have been disclosed in the prior art. For example, Japanese Patent Publication Nos. 5207/1982 and 5208/1982 disclose a liquid phase process comprising dechlorinating 1,1,2-trichlorotrifluoroethane (hereinafter referred to as "R-113") using zinc in an organic solvent, and Japanese Patent Publication No. 46049/1988 discloses a process for preparing CTFE comprising reacting R-113 and hydrogen in a gas phase in the presence of a catalyst to effect dechlorination.

In the dechlorination process using zinc, expensive zinc is used and post-treatment of zinc chloride which is by produced in a large amount is troublesome. The hydrogenation dechlorination process has the drawback that the catalyst life is short. In addition, both processes use, as a starting material, R-113, the production of which will be banned in view of its ozone destruction property.

As processes for preparing CTFE using no R-113, there are known co-pyrolysis of chlorodifluoromethane and dichlorodifluoromethane (Japanese Patent Publication No. 2132/1965) and a catalytic halogen-exchange process between tetrafluoroethylene and dichlorodifluoroethylene (hereinafter referred to as "R-1112") in the presence of a catalyst (Japanese Patent Kokai Publication No. 26239/1987). But, in the former process, the yield is low and purification of CTFE is difficult. In the latter process, R-1112 is expensive and the yield is low.

SUMMARY OF THE INVENTION

An object of the present invention is to provide a process for preparing CTFE in a high yield without using R-113 which destroys the ozone layer.

According to the present invention, there is provided a process for preparing CTFE comprising reacting tetrafluoroethylene (hereinafter referred to as "TFE") with hydrogen chloride in the presence of a metallic catalyst.

The reaction in the process of the present invention may be expressed by the reaction formula:

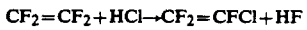

$$CF_2=CF_2+HCl \rightarrow CF_2=CFCl+HF$$

DETAILED DESCRIPTION OF THE INVENTION

In the process of the present invention, the reaction temperature is usually from 100° to 400° C., preferably from 150° to 350° C. When the reaction temperature is lower than 100° C., the conversion of TFE is low. When the reaction temperature is higher than 400° C., amounts of byproducts such as a dimer of TFE increase undesirably. In view of heat resistance of the catalyst and prevention of deterioration of catalytic activity, a more preferred reaction temperature range is 330° C. or lower.

The reaction pressure is usually from 0.1 to 100 kg/cm²G, preferably around 1 kg/cm²G.

The molar ratio of TFE to hydrogen chloride is from 0.1:1 to 10:1, preferably from 1:1 to 7:1, more preferably from 3:1 to 5:1. When the amount of TFE is too small, byproducts such as dichlorodifluoroethylene from in a larger amount. When the amount of TFE is too large, the conversion of TFE is low.

The contact time is usually from 1 to 120 seconds, preferably from 15 to 60 seconds.

The catalyst to be used according to the present invention is a metallic catalyst, which includes a metal element itself and also an oxide or halide of a metal such as chromium or aluminum. The catalyst may be used as such or supported on a carrier such as alumina, silica, activated carbon or titania. The unsupported chromium oxide catalyst is particularly preferred, since it increases the conversion of TFE so that productivity is increased. The catalyst can be produced by a per see conventional method.

Before use, the chromium oxide catalyst may be activated with at least one halogen-containing compound having at least one fluorine atom such as TFE or hydrogen fluoride. The activation of the catalyst is carried out by flowing the halogen-containing compound over the catalyst placed in a reaction tube at a comparatively high temperature, for example, about 200° to 400° C. for 1 minute to 1 hour. Together with the above halogen-containing compound, hydrogen chloride may be used.

By such activation, chromium oxide is fluorinated to give chromium oxyfluoride: $CrO_xF_y$ ($0.5x+y=3$, $0<x<1.5$, $0<y<3$), and carbon is deposited on the surface of the catalyst. Thereby, the catalyst is poisoned against the formation of the by-products, and the conversion of TFE decreases while the selectivity of CTFE increases.

The amount of carbon for poisoning the catalyst is preferably from 0.5 to 10% by weight based on the weight of $Cr_2O_3$. When the amount of carbon is smaller than 0.5% by weight, the selectivity of CTFE decreases. When it is larger than 10% by weight, the conversion of TFE decreases.

To prevent excessive deposition of carbon on the catalyst and decrease of the conversion of TFE, it is desirable to carry out the reaction at a temperature lower than the activation temperature of the catalyst.

As the reaction proceeds, the catalyst is gradually poisoned, so that the conversion of TFE gradually decreases while the selectivity of CTFE increases. When the catalyst is excessively poisoned and the conversion of TFE greatly decreases, the catalyst is regenerated by heating it in air at a temperature of 200° to 300° C.

PREFERRED EMBODIMENTS OF THE INVENTION

The present invention will be explained in detail by following Examples.

EXAMPLE 1

Using a pelletizer, chromium hydroxide powder was molded to form cylindrical pellets each having a diameter of 3 mm and a height of 3 mm. Cylindrical chromium hydroxide pellets (30 ml) were charged in a stainless steel reactor tube (a diameter of ⅜ inch and a length of 50 cm) and heated by an electric annular furnace at 350° C. with flowing nitrogen running through the tube to obtain a chromium oxide catalyst.

After poisoning the catalyst by flowing TFE at a flow rate of 45 ml/min. for 30 minutes, TFE and hydrogen chloride were run over the catalyst in the tube at flow rates shown in Table 1.

The composition of the produced gas was analyzed by gas chromatography.

The reaction conditions and the composition of the produced gas after 4 hours from the start of the reaction are shown in Table 1. The results in the parentheses are those after 24 hours from the start of the reaction. In Table 1, R-125, R-115, R-124 and R-114 represent pentafluoroethane, chloropentafluoroethane, 2-chloro-1,1,1,2-tetrafluoroethane and 1,2-dichlorotetrafluoroethane, respectively.

TABLE 1

| Temp. (°C.) | Flow rate (ml/min.) TFE | HCl | TFE conversion (%) | Selectivity (%) CTFE | R-125 | R-115 | R-124 | R-114 | R-1112 |
|---|---|---|---|---|---|---|---|---|---|
| 350 | 45 | 45 | 52 | 53 | 2 | 12 | 6 | 5 | 17 |
| 310 | 45 | 45 | 37 | 51 | 8 | 7 | 9 | 5 | 12 |
| 300 | 90 | 30 | 24(8) | 58(78) | 6(0) | 12(3) | 8(4) | 0(4) | 11(5) |
| 300 | 120 | 30 | 16(8) | 71(79) | 2(1) | 7(5) | 5(5) | 1(2) | 9(7) |
| 250 | 45 | 45 | 33(17) | 58(70) | 6(4) | 4(2) | 9(6) | 2(2) | 15(12) |

EXAMPLE 2

Activated alumina having a particle size of 2 to 4 mm (30 ml) on which 4% by weight of $CrCl_3$ was supported was charged in a stainless steel reactor tube (a diameter of ⅜ inch and a length of 50 cm) and heated and well dried by an electric annular furnace at 350° C. Over this catalyst in the tube, TFE and hydrogen chloride were run at flow rates shown in Table 2.

The composition of the produced gas was analyzed by gas chromatography.

The reaction conditions and the composition of the produced gas after 2 hours from the start of the reaction are shown in Table 2.

TABLE 2

| Temp. (°C.) | Flow rate (ml/min.) TFE | HCl | TFE conversion (%) | CTFE selectivity (%) |
|---|---|---|---|---|
| 300 | 12 | 12 | 11 | 76 |
| 350 | 12 | 12 | 27 | 74 |
| 400 | 25 | 25 | 53 | 55 |
| 400 | 45 | 45 | 45 | 59 |

EXAMPLE 3

Silica gel having a particle size of 2 to 4 mm (30 ml) on which 14% by weight of $CrCl_3$ was supported was charged in a stainless steel reactor tube (a diameter of ⅜ inch and a length of 50 cm) and heated and well dried by an electric annular furnace at 350° C. Over this catalyst in the tube, TFE and hydrogen chloride were run at flow rates shown in Table 3.

The composition of the produced gas was analyzed by gas chromatography.

The reaction conditions and the composition of the produced gas after 2 hours from the start of the reaction are shown in Table 3.

TABLE 3

| Temp. (°C.) | Flow rate (ml/min.) TFE | HCl | TFE conversion (%) | CTFE selectivity (%) |
|---|---|---|---|---|
| 300 | 17 | 12 | 6 | 75 |
| 350 | 17 | 12 | 32 | 70 |
| 400 | 17 | 12 | 67 | 54 |
| 400 | 45 | 45 | 39 | 67 |

EXAMPLE 4

Titanium oxide having a particle size of 2 to 4 mm (30 ml) on which 3% by weight of $CrCl_3$ was supported was charged in a stainless steel reactor tube (a diameter of ⅜ inch and a length of 50 cm) and heated and well dried by an electric annular furnace at 350° C. Over this catalyst in the tube, TFE and hydrogen chloride were flowed at flow rates shown in Table 4.

The composition of the produced gas was analyzed by gas chromatography.

The reaction conditions and the composition of the produced gas after 2 hours from the start of the reaction are shown in Table 4.

TABLE 4

| Temp. (°C.) | Flow rate (ml/min.) TFE | HCl | TFE conversion (%) | CTFE selectivity (%) |
|---|---|---|---|---|
| 350 | 17 | 17 | 48 | 47 |
| 400 | 45 | 45 | 55 | 42 |

EXAMPLE 5

Using a pelletizer, chromium hydroxide powder was molded to form cylindrical pellets each having a diameter of 3 mm and a height of 3 mm. Cylindrical chromium hydroxide pellets (30 ml) were charged in a stainless steel reactor tube (a diameter of ⅜ inch and a length of 50 cm) and heated by an electric annular furnace at 350° C. with flowing nitrogen running through the tube to obtain a chromium oxide catalyst.

By fluorinating the catalyst using flowing anhydrous hydrogen fluoride at a temperature of 200° to 300° C. for 2 hours, a chromium oxyfluoride catalyst was prepared. Then, TFE and hydrogen chloride were run over this catalyst in the tube at flow rates shown in Table 5.

The composition of the produced gas was analyzed by gas chromatography.

The reaction conditions and the composition of the produced gas after one hour from the start of the reaction are shown in Table 5.

TABLE 5

| Temp. (°C.) | Flow rate (ml/min.) TFE | HCl | TFE conversion (%) | CTFE selectivity (%) |
|---|---|---|---|---|
| 350 | 100 | 100 | 16 | 65 |
| 350 | 25 | 20 | 30 | 57 |
| 300 | 10 | 10 | 20 | 61 |

EXAMPLE 6

In a stainless steel reactor tube, 30 ml of activated alumina having a particle size of 2 to 4 mm was filled and heated with an annular electric heater. Over the alumina catalyst, TFE and hydrogen chloride were run to react them.

The composition of the produced gas was analyzed by gas chromatography.

The reaction conditions and the composition of the produced gas after 2 hours from the start of the reaction are shown in Table 6.

TABLE 6

| Temp. (°C.) | Flow rate (ml/min.) TFE | Flow rate (ml/min.) HCl | TFE conversion (%) | CTFE selectivity (%) |
|---|---|---|---|---|
| 400 | 70 | 240 | 1 | 30 |
| 500 | 50 | 150 | 19 | 16 |

What is claimed is:

1. A process for preparing chlorotrifluoroethylene, comprising reacting tetrafluoroethylene with hydrogen chloride in the presence of a catalyst selected from the group consisting of an oxide and a halide of chromium or aluminum.

2. The process according to claim 1, wherein the reaction temperature is in the range from 100° to 400° C.

3. The process according to claim 1, wherein the reaction pressure is in the range from 0.1 to 100 kg/cm$^2$G.

4. The process according to claim 1, wherein the contact time is in the range from 1 to 120 seconds.

5. The process according to claim 1, wherein the molar ratio of tetrafluoroethylene to hydrogen chloride is in the range from 0.1:1 to 10:1.

6. The process according to claim 1, wherein said catalyst is an oxide and/or halide of chromium.

7. The process according to claim 6, wherein said catalyst is $Cr_2O_3$.

8. The process according to claim 6, wherein said catalyst is a chromium oxyfluoride of the formula $CrO_xF_y$ wherein $0.5x+y=3$, and $0<x<5$, $0<y<3$.

9. The process according to claim 6, wherein said catalyst is poisoned with carbon in an amount of 0.5 to 10% by weight based on the weight of said catalyst.

10. The process according to claim 1, wherein said catalyst is supported on a carrier selected from the group consisting of alumina, silica, activated carbon and titania.

11. The process according to claim 2, wherein the reaction temperature is in the range from 150° to 350° C.

12. The process according to claim 2, wherein the reaction temperature is 330° C. or lower.

13. The process according to claim 3, wherein the reaction pressure is about 1 kg/cm$^2$G.

14. The process according to claim 5, wherein the molar ratio of tetrafluoroethylene to hydrogen chloride is in the range from 1:1 to 7:1.

15. The process according to claim 5, wherein the molar ratio of tetrafluoroethylene to hydrogen chloride is in the range from 3:1 to 5:1.

16. The process according to claim 4, wherein the contact time is in the range from 15 to 60 seconds.

17. The process according to claim 1, wherein said catalyst is used as such, or is supported on a carrier.

18. The process according to claim 7, wherein said $Cr_2O_3$ is unsupported.

19. The process according to claim 7, wherein said $Cr_2O_3$ is activated before use with at least one halogen-containing compound containing at least one fluorine atom, and optionally, hydrogen chloride.

20. The process according to claim 19, wherein said halogen-containing compound containing at least one fluorine atom is a member selected from the group consisting of tetrafluoroethylene and hydrogen fluoride.

21. The process according to claim 19, wherein said $Cr_2O_3$ is activated by allowing said halogen-containing compound to flow over said $Cr_2O_3$ at a temperature of about 200° to 400° C. for 1 minute to 1 hour.

22. The process according to claim 1, wherein said catalyst is regenerated by heating it in air at a temperature of 200° to 300° C.

* * * * *